United States Patent
Murao

(10) Patent No.: US 6,925,199 B2
(45) Date of Patent: Aug. 2, 2005

(54) COMPUTER READABLE RECORDING MEDIUM RECORDED WITH DIAGNOSIS SUPPORTING PROGRAM, DIAGNOSIS SUPPORTING APPARATUS AND DIAGNOSIS SUPPORTING METHOD

(75) Inventor: Kohei Murao, Kawasaki (JP)

(73) Assignee: Fujitsu Limited, Kawasaki (JP)

(*) Notice: Subject to any disclaimer, the term of this patent is extended or adjusted under 35 U.S.C. 154(b) by 467 days.

(21) Appl. No.: 09/818,549

(22) Filed: Mar. 28, 2001

(65) Prior Publication Data

US 2002/0065460 A1 May 30, 2002

(30) Foreign Application Priority Data

Nov. 29, 2000 (JP) ........................................ 2000-362779

(51) Int. Cl.⁷ ................................................ G06K 9/00
(52) U.S. Cl. ............................ 382/131; 382/305; 707/6
(58) Field of Search .................. 382/128, 131–133, 382/190, 291, 305, 209, 217, 208; 707/6

(56) References Cited

U.S. PATENT DOCUMENTS 5,836,872 A * 11/1998 Kenet et al. ................. 600/306
6,075,879 A * 6/2000 Roehrig et al. .............. 382/132
6,292,577 B1 * 9/2001 Takahashi .................... 382/128

OTHER PUBLICATIONS

"Computer Aided Diagnosis System for Lung Cancer Based on Helical CT Images" by Kanazawa et al., IEEE, Pattern Recognition, 1996., Proceedings of the 13th International Conference on , vol.: 3 , Aug. 25–29, 1996.*

N. Niki, "System for Aiding CT Image Diagnosis for Lung Cancer ", Japanese Radiation Technological Academy Magazine, vol. 56, No. 3, Mar. 2000, pp. 337–340.

M. Kondo, "Classification of tumors in chest X–ray CT Images into the solid and air–containing type and its application to discrimination of the benign and malignant tumors", Technical Report of IEICE M12000–16, May 2000, pp. 27–32.

* cited by examiner

Primary Examiner—Jon Chang
Assistant Examiner—Charles Kim
(74) Attorney, Agent, or Firm—Staas & Halsey LLP

(57) ABSTRACT

A computer readable recording medium recorded with a diagnosis supporting program, a diagnosis supporting apparatus and a diagnosis supporting method, enabling to retrieve similar disease cases making use of feature quantities of CT images and/or MRI images when interpreting such images, to thereby allow an improvement of diagnosis precision.

19 Claims, 8 Drawing Sheets

FIG.2

| PATIENT ID | INSPECTION ID | IMAGE FILE NAME |
|---|---|---|
| 0001 | 01 | xxxx.dcm |
| 0002 | 02 | yyyy.dcm |
| .... | .. | ..... |

FIG.3

| TARGET SITE | INSPECTION DATE | FEATURE DATE |
|---|---|---|
| BRAIN | 2000/11 | aaaaaaaa |
| CHEST | 2000/11 | bbbbbbbb |
| ABDOMEN | 2000/11 | cccccccc |
| HAUNCHES | 2000/11 | dddddddd |
| LEG | 2000/11 | eeeeeeee |
| ... | .... | ..... |

FIG.4

| PATIENT ID | INSPECTION ID | ASSIGNED DOCTOR NAME | FINDINGS |
|---|---|---|---|
| 0001 | 01 | xxxx | aaaaaaaa |
| 0002 | 02 | yyyy | bbbbbbbb |
| .... | .. | .... | .... |

FIG.9

| ORGAN | VOLUME | AVERAGED CT VALUE | TEXTURE | SPHERICAL DEGREE | ... |
|---|---|---|---|---|---|
| BRAIN | $w_{11}$ | $w_{12}$ | $w_{13}$ | $w_{14}$ | ... |
| LUNG | $w_{21}$ | $w_{22}$ | $w_{23}$ | $w_{24}$ | ... |
| LIVER | $w_{31}$ | $w_{32}$ | $w_{33}$ | $w_{34}$ | ... |
| ... | ... | ... | ... | ... | ... |

FIG.10

| ORDER | DISEASE NAME | PROBABILITY |
|-------|--------------|-------------|
| 1 | DIEASE NAME A | 60% |
| 2 | DIEASE NAME B | 22% |
| 3 | DIEASE NAME C | 18% |

FIG.11

| ORDER | INSPECTION ID | SIMILARITY | DISEASE NAME |
|-------|---------------|------------|--------------|
| 1 | INSPECTION 5 | 90% | DISEASE NAME A |
| 2 | INSPECTION 2 | 87% | DISEASE NAME B |
| 3 | INSPECTION 1 | 81% | DISEASE NAME A |
| 4 | INSPECTION 7 | 70% | DISEASE NAME C |
| 5 | INSPECTION 9 | 69% | DISEASE NAME A |
| 6 | INSPECTION 8 | 33% | DISEASE NAME D |
| ...... | | | |

COMPUTER READABLE RECORDING MEDIUM RECORDED WITH DIAGNOSIS SUPPORTING PROGRAM, DIAGNOSIS SUPPORTING APPARATUS AND DIAGNOSIS SUPPORTING METHOD

FIELD OF THE INVENTION

The present invention relates to a technique for improving diagnosis precision particularly in a diagnosis supporting technique for supporting diagnoses by image interpretation.

RELATED ART OF THE INVENTION

There have been conventionally conducted interpretation of CT (Computerized Tomography) images and MRI (Magnetic Resonance Imaging) images, for example, by subjective estimations based on experiences stored over time by doctors such as radiologists. However, image diagnoses based on only subjective estimations fail to avoid misdiagnoses such as due to oversight and/or misunderstanding. To avoid such misdiagnoses, various endeavors have been made such as by interpreting CT images by a plurality of doctors. However, many problems are still left such as due to the restriction of time.

Meanwhile, digitization of CT images has been intensely developed at present, such that almost all CT images are digitized in the fields of from simple photographs to angiographic images. Further, there has been developed a PACS (Picture Archiving and Communication System) for quickly transmitting and accumulating images, so that all of the digitized CT images can be useful.

In interpreting CT images, it is also known that the diagnosis precision is improved by referring to CT images of similar disease cases among those CT images photographed in the past. However, it has been extremely difficult to select suitable reference images out of a great deal of stored CT images, since the conventional PACS merely allows to accumulate and refer to digital images. As such, irrespective of the development of the PACS, since those CT images photographed in the past have not been fully utilized, diagnoses based on subjective estimations by doctors have been still conducted, resulting in a situation difficult for an improvement of diagnosis precision.

The present invention has been carried out in view of the conventional problems as described above, and it is therefore an object of the present invention to provide a diagnosis supporting technique for enabling a search for similar disease cases by using feature quantities of CT images when interpreting them, to thereby allow an improvement of diagnosis precision.

SUMMARY OF THE INVENTION

To this end, the diagnosis supporting technique according to the present invention is characterized in that image-wise feature quantities of a lesion position detected in a diagnosis target image are extracted, and reference images which are image-wise similar to the diagnosis target image is retrieved out of a database stored with reference images and feature quantities thereof, based on the extracted feature quantities, from.

According to such a constitution, reference images which are image-wise similar to the diagnosis target image are retrieved from those reference images stored in the database, based on the feature quantities of the lesion position detected from the diagnosis target image. Thus, a doctor to conduct diagnosis by interpreting the diagnosis target image is possible to readily refer to those past disease cases similar to the disease case of the lesion portion appearing in the diagnosis target image. This allows objective diagnosis excluding the subjectivity. Since the objective diagnosis becomes possible, there can be drastically reduced the possibility of misdiagnosis even by a less experienced doctor, for example, to thereby enable an improvement of diagnosis precision. Further, even when a disease name of the diagnosis target image is unclear from the diagnosis target image only, the disease name can be estimated by utilization of reference disease cases, to thereby improve diagnosis precision.

In this case, it is preferable to register the diagnosis target image and the feature quantities thereof into the database. In this way, the once diagnosed diagnosis target image and the feature quantities thereof are registered into the database, so that the diagnosis target image and feature quantities thereof are turned to be a retrieval target as a reference image and feature quantities thereof in later diagnoses. Thus, the reference data are progressively strengthened as the interpretation of diagnosis target images is progressed.

Further, it is preferable to calculate image-wise similarities between each of the reference images stored in the database and the diagnosis target image, respectively, by matching the feature quantities of each of the reference images stored in the database with the feature quantities of the diagnosis target image, and to retrieve reference images in order of similarity. Here, it is preferred that the similarity is calculated taking account of the weighting set for each organ, and the weighting is set in a variably constituted table.

According to such a constitution, similarities between the diagnosis target image and each of the reference images are defined based on the image-wise similarities, respectively, so that reference images are sequentially retrieved from those having higher similarities. Thus, those reference images having higher possibilities of usefulness are referred to when interpreting the diagnosis target image, to thereby avoid useless reference and to thereby improve the diagnosis efficiency. Here, if the similarities are calculated taking account of the weighting set for each organ, similarities corresponding to the characteristic of each organ are calculated, to thereby improve calculation precision of similarities. If the variably constituted table is set with the weighting, it becomes possible to conduct, for example, a correction corresponding to peculiar characteristics of a CT apparatus, thereby further improving the calculation precision of similarities.

Further, it is preferable to display the findings related to the retrieved reference images. In this way, the findings of the reference images can be referred to in addition to the reference images themselves, so that, even when a disease name for a patient is unclear, such a disease name can be diagnosed from the findings of similar disease cases.

In addition, it is possible to detect a lesion position of a designated organ, when detecting the lesion position from the diagnosis target image. Further, it is possible to extract, as the image-wise feature quantities, a global feature quantity, a topical feature quantity and a common feature quantity, for every lesion position of the diagnosis target image.

According to such a constitution, the detecting procedures for organs which are not diagnosis targets are avoided, to thereby improve the processing speed. Further, by detecting, as the image-wise feature quantities, the global feature quantity, the topical feature quantity and the common feature quantity, it becomes possible to extract feature quantities corresponding to characteristics of each disease, thereby preventing oversight of a tumor, for example.

Other objects and features of the present invention will become more apparent from the following description of a preferred embodiment when read in conjunction with the accompanying drawings.

BRIEF EXPLANATION OF THE DRAWINGS

FIG. 2 is an explanatory view of an index of an image DB (database);

FIG. 3 is an explanatory view of an index of a feature DB;

FIG. 4 is an explanatory view of an index of a finding DB;

FIG. 9 is an explanatory view of a weighting vector table;

FIG. 10 is an explanatory view of a screen for displaying disease names and probabilities thereof; and FIG. 11 is an explanatory view of reference disease cases aligned in order of similarity.

PREFERRED EMBODIMENT

The present invention will be described hereinafter with reference to the accompanying drawings.

Figure 1:
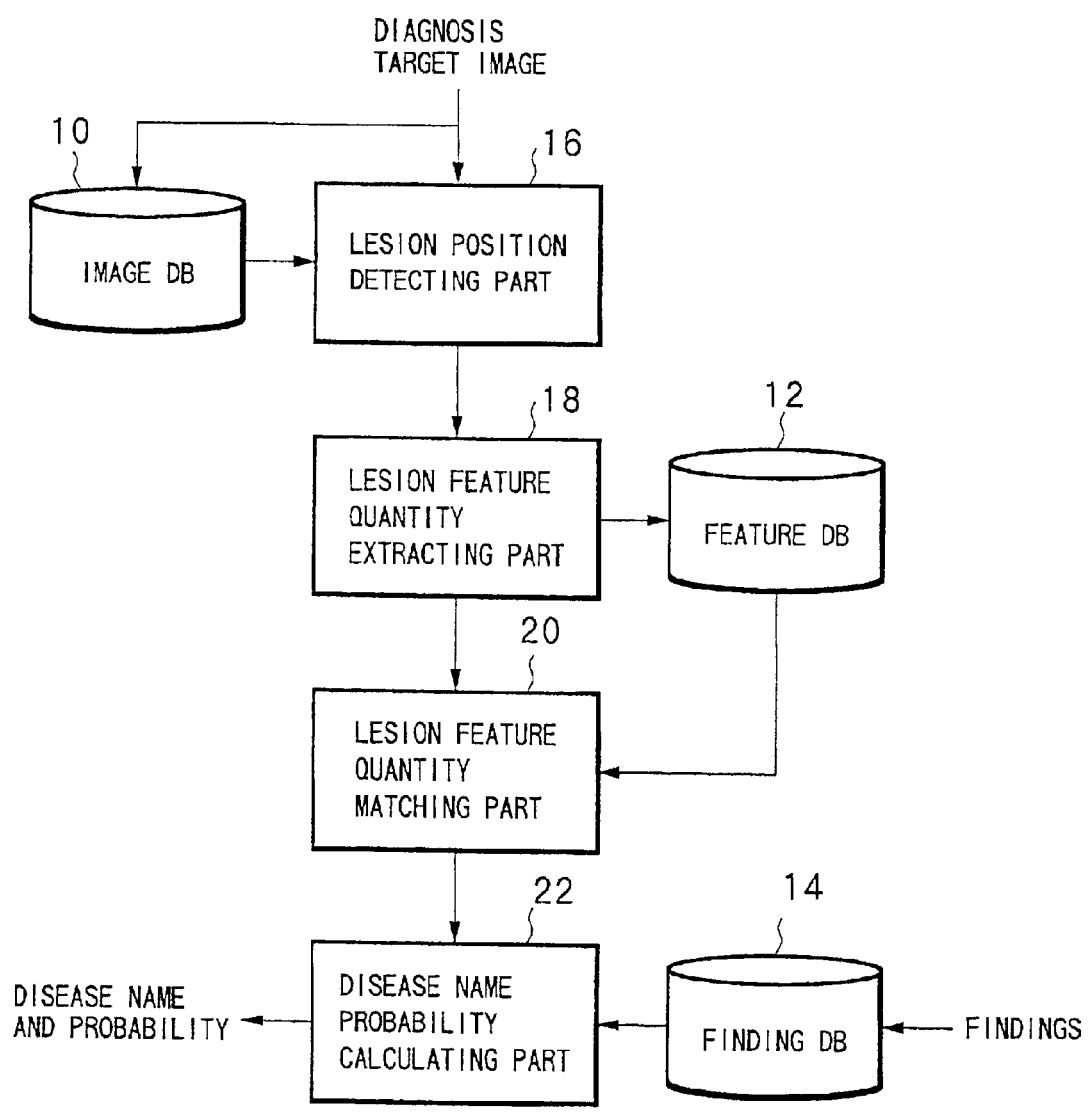
FIG. 1 is a constitutional diagram of a diagnosis supporting apparatus according to the present invention.

FIG. 1 shows a constitution of a diagnosis supporting apparatus realizing the diagnosis supporting technique according to the present invention. The diagnosis supporting apparatus is constructed on a computer system comprising at least a central processing unit (CPU) and a memory, and operates according to a program loaded onto the memory.

The diagnosis supporting apparatus comprises an image database 10, a feature database 12, a finding database 14, a lesion position detecting part 16, a lesion feature quantity extracting part 18, a lesion feature quantity matching part 20 and a disease name probability calculating part 22. Note, the term "database" shall be abbreviated to "DB" in the following description.

Stored in the image DB 10 are image data such as CT images and MRI images in the format in accordance with DICOM (Digital Imaging and Communications in Medicine). Here, the DICOM means standards concerning digital imaging and communications in medicine, which have been developed in the United States and adopted also in Japan. Further, to relate the image DB 10, feature DB 12 and finding DB 14 to one another, an index of the image DB 10 is registered with at least a patient ID, an inspection ID and an image file name, as shown in FIG. 2. Note, the DICOM header of each image file is registered with information such as an inspection date and a target site (i.e., name of organ).

Stored in the feature DB 12 are lesion feature quantities extracted from the image data. The lesion feature quantities are information for enabling a retrieval of image data by utilizing image-wise similarities, and include a lesion size (volume or area), a shape (spherical degree or circular degree), a brightness statistic (such as average and/or a deviation), and a texture statistic (such as spatial frequency resolution, Fourier transform, and wavelet transform). The lesion feature quantities are bundled into feature data related to the patient ID and the inspection ID. Further, an index of the feature DB 12 is registered with at least a target site, an inspection date and feature data of pertinent, as shown in FIG. 3. Here, it will take a long time to get file access when retrieving, if the feature data and the image data are divided to correspond to each other in a one-to-one corresponding manner. Thus, it is desirable to unify the feature data such as in a month unit. In this case, there are registered only a year and a month, as an inspection date. Further, the feature data is divided for each target site to improve the retrieval efficiency.

Stored in the finding DB 14 are findings that are interpretation results of CT images. An index of the finding DB 14 is registered with at least the patient ID, the inspection ID, an assigned doctor name, and findings, as shown in FIG. 4. Note, the findings include at least a disease name diagnosed by interpreting a CT image.

At the lesion position detecting part 16, a lesion position (s) in the organ or site to be diagnosed (hereinafter simply called "organ") is detected from a CT image. Detection of lesion position is conducted such as by the technique shown in "Lung cancer CT medical examination supporting system" by N. Niki, in the Japanese radiation technological academy magazine, Vol. 56 No. 3, March (2000), pp. 337–340.

At the lesion feature quantity extracting part 18, lesion feature quantities representing image-wise similarities by statistics are extracted, for all of the lesion positions detected by the lesion position detecting part 16. Extraction of lesion feature quantities is conducted such as by the technique shown in "Classification of tumor shadows in 3-dimensional chest X-ray CT image into pneumatic type and solid type, and its Application to discrimination between benignant and malignant natures" by M. Kondo, in the Technical Report of IEICE M12000-16 (2000-05), pp. 27–32.

At the lesion feature quantity matching part 20, the lesion feature quantities extracted by the lesion feature quantity extracting part 18 and the lesion feature quantities stored in the feature DB 12 are mutually matched for the organ as a diagnosis target, to thereby calculate a similarity representing a criterion of image-wise similarity.

At the disease name probability calculating part 22, probabilities of disease names of the organ as the diagnosis target are calculated, based on the similarities calculated by the lesion feature quantity matching part 20. Then, the disease names and probabilities thereof are displayed in a display device (not shown), to thereby support the doctor in conducting diagnosis.

There will be explained hereinafter an outline of the diagnosis supporting apparatus having the aforementioned constitution.

When tomograms are taken by an X-ray CT apparatus, CT images are stored in the image DB 10 and the lesion positions are detected by the lesion position detecting part 16. When the lesion positions are detected, lesion feature quantities are extracted for all of the lesion positions. The thus extracted lesion feature quantities are registered into the feature DB 12, and calculated the similarities thereof with those of the CT images concerning the past disease cases as stored in the feature DB 12 by the lesion feature quantity matching part 20. Then, probabilities of disease names corresponding to the similarities of the CT images are calculated by the disease name probability calculating part 22, and these probabilities are represented to the doctor together with disease names in order of probability.

Thus, the doctor to conduct diagnosis by interpreting a CT image becomes possible to readily refer to those past disease cases which are similar to the disease case at issue as the diagnosis target, and also possible to conduct objective diagnosis excluding the subjectivity by referring to the findings of the past disease cases. At this time, since both disease names and probabilities for the disease case as the diagnosis target are displayed, even when a disease name of a patient is unclear, it becomes possible to diagnose the disease name of such a disease case by referring to the displayed disease names and probabilities thereof. In this way, diagnosis precision by a doctor can be improved.

Figure 5:
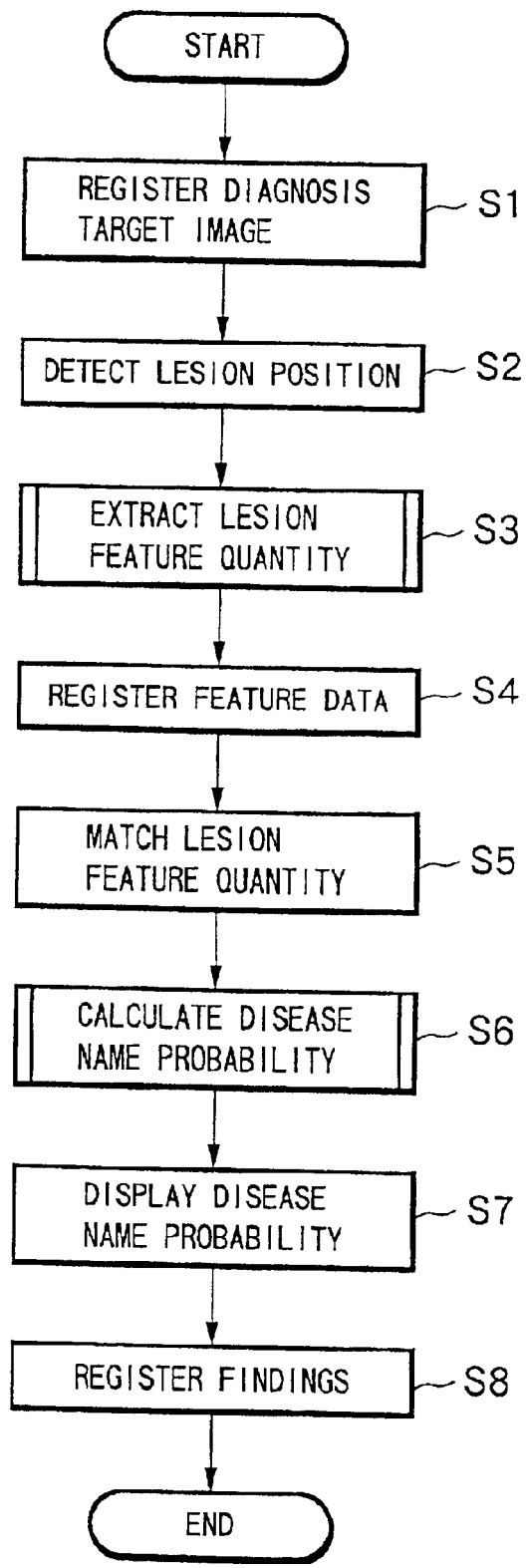
FIG. 5 is a flowchart of a main routine showing the controlling details.
Figure 6:
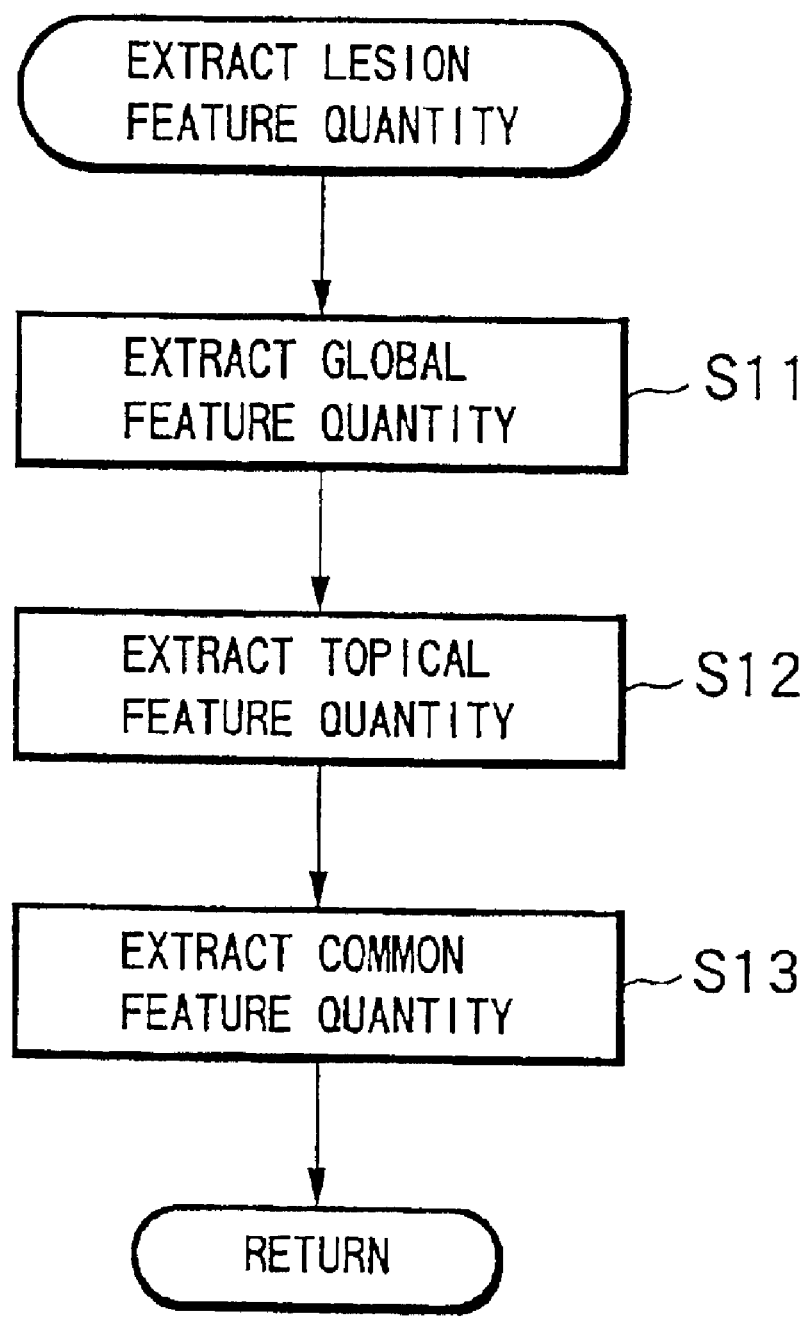
FIG. 6 is a flowchart of a sub-routine for extracting lesion feature quantities.
Figure 7:
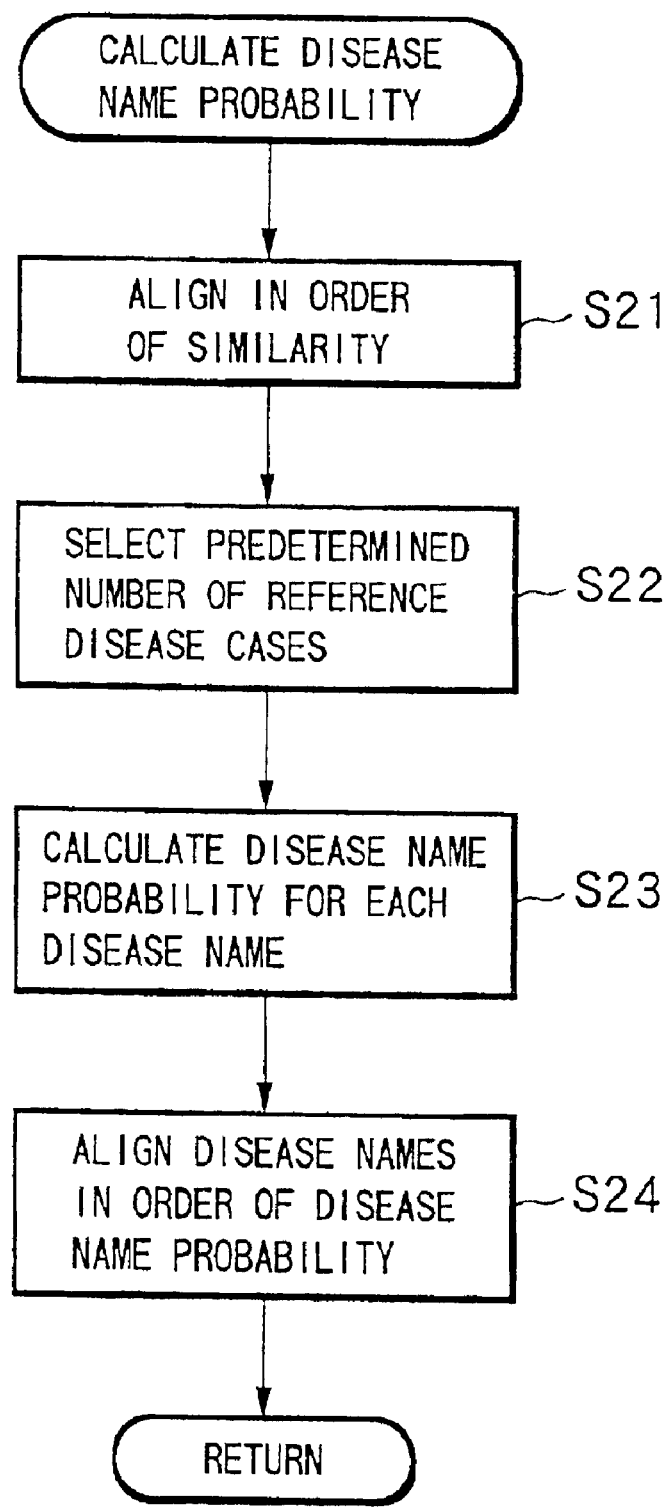
FIG. 7 is a flowchart of a sub-routine for calculating a disease name probability.

FIGS. 5 through 7 show flowcharts showing the control details of the diagnosis supporting apparatus. Note, such a control is executed after a CT image is photographed by the X-ray CT apparatus, and then an organ is designated and a patient ID and an inspection ID are input.

In FIG. 5 showing a main routine, the photographed CT image (hereinafter called "diagnosis target image") is registered into the image DB 10 at step 1 (abbreviated to "S1" in the figure, and the same rule applies corresponding to the following). At this time, the index of the image DB 10 is additionally registered with a patient ID, an inspection ID and an image file name, so as to specify the registered image by relating the same to the patient ID and inspection ID. Note, the procedure at step 1 corresponds to a part of each of a database registering function, database registering means and a database registering process.

At step 2, a lesion position in the designated organ is detected from the diagnosis target image, by the function provided by the lesion position detecting part 16. Namely, the contour of the organ is detected by applying a filtering treatment, such as refining or morphology based on brightness value or CT value, to the diagnosis target image. Next, there are calculated differences indicating what degrees the detected contour of the organ is deviated from a normal region. The normal region of organ is defined by being supposed to be an inner contour of ribs, such as in case of a lung. Further, those portions where the calculated differences are predetermined widths or more are regarded as lesion positions.

Meanwhile, in case of a topical lesion such as a tumor, the lesion position is detected such as by searching for a spherical portion having a higher brightness and a diameter equal to or less than a predetermined value. Note, those tumors contacting with a blood vessel or a trachea can be detected by combining thinning and spherical portion searching.

Further, since an estimation of a lesion position may vary from doctor to doctor, it is preferable to provide such a function to modify, delete and add the lesion position.

The procedure at step 2 corresponds to a lesion position detecting function, lesion position detecting means and a lesion position detecting process.

At step 3, there is called a sub-routine as shown in FIG. 6 for extracting lesion feature quantities, so as to extract lesion feature quantities for all of the detected lesion positions. Note, the procedure at step 3, i.e., the whole procedure in FIG. 6 corresponds to a feature quantity extracting function, feature quantity extracting means and a feature quantity extracting process.

At step 4, the extracted lesion feature quantities are registered into the feature DB 12. At this time, the lesion feature quantities are incorporated into and unified into a piece of feature data corresponding to the target site and the inspection date, for improving the retrieval efficiency. However, when the inspection date is different from that already registered or when no corresponding feature data have been registered, the index of the feature DB 12 is additionally registered with the new target site, the new inspection date and a new piece of feature data. Note, the procedure at step 4 corresponds to a part of each of a database registering function, database registering means and a database registering process.

Figure 8:
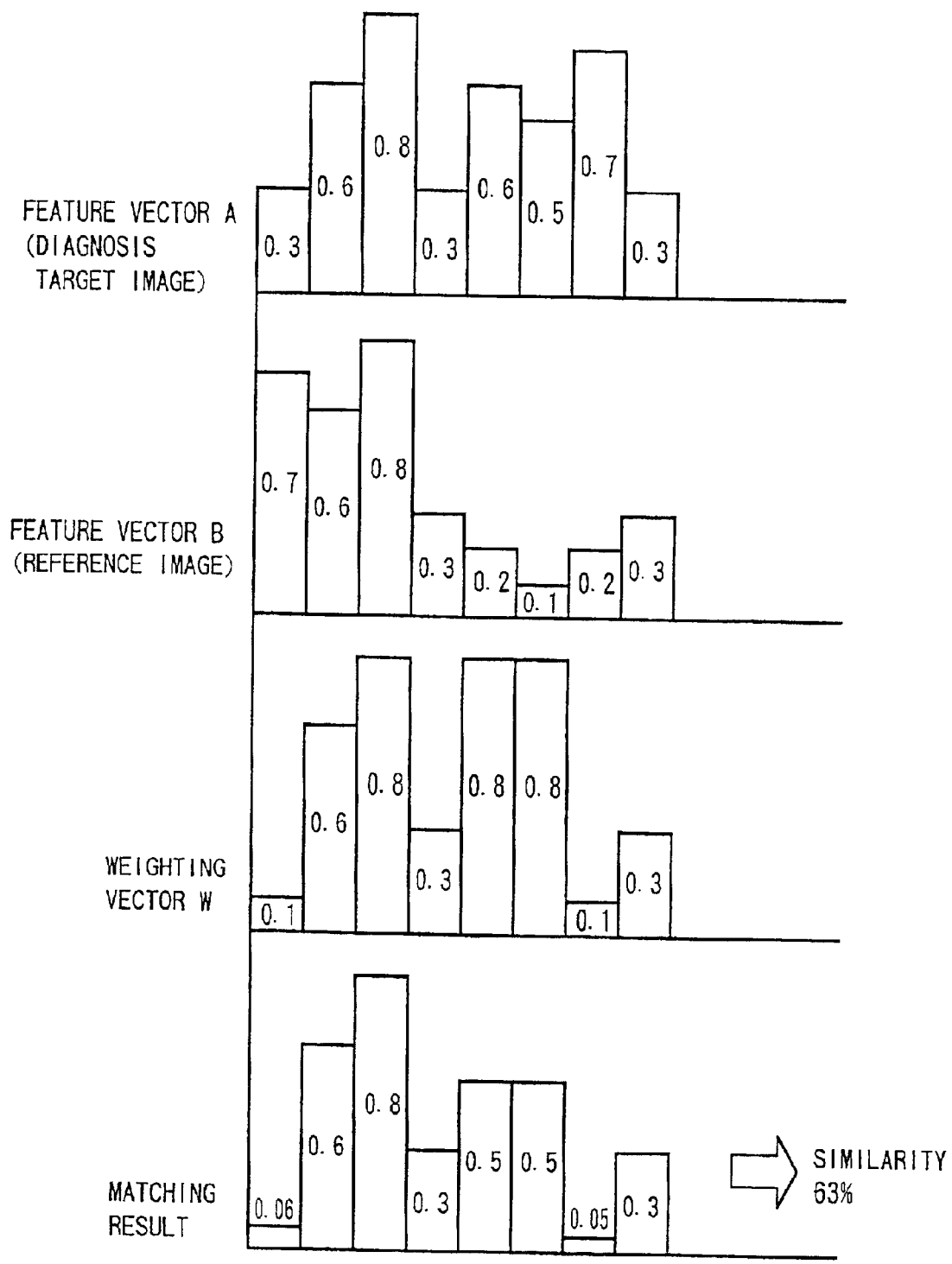
FIG. 8 is an explanatory view of a method for calculating a similarity.

At step 5, the lesion feature quantities of the diagnosis target image are matched with lesion feature quantities stored in the feature DB 12 concerning the diagnosis target organ by the function provided by the lesion feature quantity matching part 20, so as to calculate the similarities of the stored CT images (hereinafter called "reference images"). Namely, as shown in FIG. 8, the lesion feature quantities of the diagnosis target image and of the reference image are arranged in a vector manner from a first element in each image unit (inspection unit), such as a volume, an average of brightness, a deviation of brightness, a spherical degree, a texture statistic, and so on. Each element is normalized to be in a range from 0 to 1, so as to be compared at the same level. Concerning a volume for example, when the target site is a lung, the volume of a lesion portion can be normalized since the volume of the lesion portion is necessarily smaller than the volume of the lung.

Then, defining two feature vectors A and B as:

$A=(f_1 f_2 f_3 \ldots)$ $B=(g_1 g_2 g_3 \ldots)$ while assuming a weighting vector W as:

$W=(w_1 w_2 w_3 \ldots)$, there can be calculated a similarity S as follows:

$$S = W^t(E-(A-B))/|W|$$

$$= [w_1(1-f_1+g_1) + w_2(1-f_2+g_2) + \ldots]/(w_1+w_2+\ldots),$$

wherein E is a vector all components of which are zero, and |W| is a sum of all components of the weighting vector W. It is preferable that the weighting vector W is set in a table form for each organ as shown in FIG. 9.

It is also preferable that respective components of the weighting vector W can be freely modified by a user. It is possible to previously study the correspondence between lesion feature quantities and findings a neural network, so as to set the optimum weighting value.

The procedure at step 5 corresponds to a reference image retrieving function, reference image retrieving means, a reference image retrieving process, a similarity calculating function, similarity calculating means, and a similarity calculating process.

At step 6, there is called a sub-routine as shown in FIG. 7 for calculating disease name probabilities, so as to calculate probabilities of disease names of the lesion portion appearing in the diagnosis target image.

At step 7, disease names and probabilities thereof are displayed in a screen such as shown in FIG. 10. Note, the procedure at step 7 corresponds to a finding displaying function, finding displaying means and a finding displaying process.

At step 8, the findings being the final diagnosis result of a doctor are registered into the finding DB 14. At this time, the doctor is possible to conduct objective diagnosis while eliminating the subjectivity, by referring to the reference images and findings thereof, in addition to the diagnosis target image as well as those disease names and probabilities thereof which have been estimated from the diagnosis target image. Further, those findings registered at this step are to be utilized as the findings of the reference images in later diagnoses, to thereby strengthen the data for supporting diagnosis, as the number of registered findings increases.

Note, it is preferable to register reference images, feature data and findings representing typical disease cases into respective DB's as their initial states, since no reference images, no feature data and no findings have been stored when starting the operation of the diagnosis supporting apparatus.

FIG. 6 shows the aforementioned sub-routine for extracting lesion feature quantities. Note, extraction of the lesion feature quantities is conducted by the function provided by the lesion feature quantity extracting part 18.

At step 11, a global feature quantity for a lesion portion over a wide area is extracted. Namely, a texture statistic as a global feature quantity is extracted for the whole of the detected lesion portion, such as by applying thereto a spatial frequency resolution, Fourier transform, or wavelet transform.

At step 12, a topical feature quantity for a lesion portion limited within a topical area is extracted. Namely, a spherical degree (in 3-dimension) or circular degree (in 2-dimension), for example, is extracted for the detected topical lesion portion.

At step 13, common feature quantities common to lesion portions are extracted. Namely, a size (volume or area) and a brightness statistic (such as average, deviation), for example, are extracted for the detected lesion portion.

FIG. 7 shows the aforementioned sub-routine for calculating disease name probabilities. Note, the calculation of the disease name probabilities is conducted by the function provided by the disease name probability calculating part 22.

At step 21, those feature data stored in the feature DB 12 the similarities of which have been calculated are aligned as shown in FIG. 11 in order of similarity, while being bundled each order, inspection ID, similarity and disease name into a row. At this time, each disease name can be obtained from the findings, by retrieving the finding DB 14 while using the patient ID and the inspection ID included in the feature data as keys.

At step 22, those pieces of feature data, which are within the top 10 positions or each of which has a similarity of 50% or more, for example, are selected from the feature data aligned in order of similarity, as reference disease cases to be useful for conducting diagnosis for the diagnosis target image.

At step 23, a disease name probability in which similarities has been averaged for each disease name is calculated, for all of the selected reference disease cases.

At step 24, disease names and probabilities thereof are displayed in order of disease name probability.

Note, if the correspondence between lesion feature quantities and findings has been studied by the neural network, it is possible to directly calculate a disease name and probability thereof from lesion feature quantities.

According to the diagnosis supporting apparatus as explained above, lesion positions are detected from a diagnosis target image concerning a designated organ, and lesion feature quantities at all of the detected lesion positions are extracted. The extracted lesion feature quantities are matched with the feature data concerning the same organ stored in the feature DB 12, so as to calculate similarities of disease cases that may later become reference images. Then, disease names and probabilities thereof are calculated, respectively, based on the calculated similarities, to be displayed on the display device.

Thus, the doctor to conduct diagnosis by interpreting a diagnosis target image is possible to refer to those past disease cases that are similar to the lesion portion appearing in the diagnosis target image, to thereby conduct objective diagnosis excluding the subjectivity. Since the objective diagnosis becomes possible, there can be drastically reduced the possibility of misdiagnosis even by a less experienced doctor, for example, to thereby enable an improvement of diagnosis precision. Further, even when a disease name is unclear from the diagnosis target image only, by utilizing reference disease cases, it is possible to estimate the disease name of the diagnosis target image to thereby improve diagnosis precision.

Further, the diagnosis target image the diagnosis of which has been completed is registered into the database together with the lesion feature quantities and findings thereof, so as to be later utilized as a reference image. Thus, the reference data are progressively strengthened as the interpretation of diagnosis target images is progressed, to thereby further improve the diagnosis precision.

Although the diagnosis supporting apparatus in this embodiment has been constructed on a computer system of stand-alone type, it may be constructed on client/server models connected via a network. In this case, reference disease cases can be stored on the whole nation scale or the global scale, to thereby contribute to improvement of medical technique, and to be extremely useful from the standpoint of the public benefit.

By recording a program for realizing such functions into a computer readable recording medium such as a magnetic tape, a magnetic disk, a magnetic drum, an IC card, a CD-ROM, and a DVD-ROM, the diagnosis supporting program according to the present invention can be distributed into the market. Further, those who have obtained such a recording medium are possible to readily construct the diagnosis supporting apparatus according to the present invention, making use of a general computer system.

What is claimed:

1. A computer readable recording medium storing a diagnosis supporting program for controlling a computer, said program performing:

detecting a lesion position from a diagnosis target image;

extracting image-wise feature quantities of the lesion position detected by said detecting;

retrieving reference images which are image-wise similar to the diagnosis target image out of a database stored with reference images and feature quantities of reference images, based on said extracting; and calculating image-wise similarities between each of the reference images stored in the database and the diagnosis target image, respectively, by matching the feature quantities of each of the reference images stored in the database with the feature quantities of the diagnosis target image, wherein the diagnosis target image and the reference images comprise at least one of CT images and MRI images, wherein said retrieving retrieves reference images in order of similarity as calculated by said calculating, wherein said calculating calculates similarities, taking into account a weighting set for each organ; and wherein the weighting set is set so as to correspond to the feature quantities of each of a plurality of organs and the corresponding reference images.

2. A computer readable recording medium according to claim 1, further comprising:

registering the diagnosis target image and the feature quantities thereof into the database.

3. A computer readable recording medium according to claim 1, wherein said weighting is set in a variably constituted table.

4. A computer readable recording medium according to claim 1, further comprising:

displaying findings related to the reference images retrieved by said retrieving.

5. A computer readable recording medium according to claim 1, wherein said detecting detects a lesion position of a designated organ.

6. A computer readable recording medium according to claim 1, wherein said extracting extracts a global feature quantity, a topical feature quantity and a common feature quantity, for every lesion position of the diagnosis target image.

7. A diagnosis supporting apparatus comprising:

lesion position detecting means for detecting a lesion position from a diagnosis target image;

feature quantity extracting means for extracting image-wise feature quantities of the lesion position detected by said lesion position detecting means;

reference image retrieving means for retrieving reference images which are image-wise similar to the diagnosis target image out of a database stored with reference images and feature quantities of reference images, based on the feature quantities extracted by said feature quantity extracting means; and similarity calculating means for calculating image-wise similarities between each of the reference images stored in said database and the diagnosis target image, respectively, by matching the feature quantities of each of the reference images stored in said database with the feature quantities of the diagnosis target image, wherein the diagnosis target image and the reference images comprise at least one of CT images and MRI images;

wherein said reference image retrieving means retrieves reference images in order of similarity as calculated by said similarity calculating means, wherein said similarity calculating means calculates similarities, taking into account a weighting set for each organ, and wherein the weighting set is set so as to correspond to the feature quantities of each of a plurality of organs and the corresponding reference images.

8. A diagnosis supporting apparatus of claim 7, further comprising:

database registering means for registering said diagnosis target image and feature quantities thereof into said database.

9. A diagnosis supporting apparatus of claim 7, wherein said weighting is set in a variably constituted table.

10. A diagnosis supporting apparatus of claim 7, further comprising:

finding displaying means for displaying findings related to the reference images retrieved by said reference image retrieving means.

11. A diagnosis supporting apparatus of claim 7, wherein said lesion position detecting means detects a lesion position of a designated organ.

12. A diagnosis supporting apparatus of claim 7, wherein said feature quantity extracting means extracts a global feature quantity, a topical feature quantity and a common feature quantity, for every lesion position of the diagnosis target image.

13. A diagnosis supporting method comprising:

a lesion position detecting process for detecting a lesion position from a diagnosis target image;

a feature quantity extracting process for extracting image-wise feature quantities of the lesion position detected by said lesion position detecting process;

a reference image retrieving process for retrieving reference images which are image-wise similar to the diagnosis target image out of a database stored with reference images and feature quantities of reference images, based on the feature quantities extracted by said feature quantity extracting process; and a similarity calculating process for calculating image-wise similarities between each of the reference images stored in said database and the diagnosis target image, respectively, by matching the feature quantities of each of the reference images stored in said database with the feature quantities of the diagnosis target image, wherein the diagnosis target image and the reference images comprise at least one of CT images and MRI images;

wherein said reference image retrieving process retrieves reference images in order of similarity as calculated by said similarity calculating process, wherein said similarity calculating process calculates similarities, taking into account a weighting set for each organ, and wherein the weighting set is set so as to correspond to the feature guantities of each of a plurality of organs and the corresponding reference images.

14. A diagnosis supporting method of claim 13, further comprising:

a database registering process for registering said diagnosis target image and feature quantities thereof into said database.

15. A diagnosis supporting method of claim 13, wherein said weighting is set in a variably constituted table.

16. A diagnosis supporting method of claim 13, further comprising:

a finding displaying process for displaying findings related to the reference images retrieved by said reference image retrieving process.

17. A diagnosis supporting method of claim 13, wherein said lesion position detecting process detects a lesion position of a designated organ.

18. A diagnosis supporting method of claim 13, wherein said feature quantity extracting process extracts a global feature quantity, a topical feature quantity and a common feature quantity, for every lesion position of the diagnosis target image.

19. A diagnosis supporting method comprising:

detecting a lesion position from a target image;

extracting image-wise feature quantities of the detected lesion position;

retrieving reference images which are image-wise similar to a target image out of a database storing reference images and feature quantities of reference images, based on the extracted feature quantities; and calculating image-wise similarities between each of the reference images and the target image by matching the feature quantities of each of the reference images with the feature quantities of the target image, wherein the reference images are retrieved in order of similarity as calculated by said calculating image-wise similarities, and wherein said calculating comprises calculating similarities, taking into account a weighting set for each organ, wherein the target image and the reference images comprise at least one of CT images and MRI images, and wherein the weighting set is set so as to correspond to the feature quantities of each of a plurality of organs and the corresponding reference images.

* * * * *

UNITED STATES PATENT AND TRADEMARK OFFICE
CERTIFICATE OF CORRECTION

PATENT NO. : 6,925,199 B2  Page 1 of 1
APPLICATION NO. : 09/818549
DATED : August 2, 2005
INVENTOR(S) : Kohei Murao It is certified that error appears in the above-identified patent and that said Letters Patent is hereby corrected as shown below:

Cover Page, column 2, line 7, change "Aug. 25-29, 1996." to --Aug. 25-29, 1996, pp. 381-385, Vol. 3.--

Column 11, line 21, in claim 13, change "guantities" to --quantities--

Signed and Sealed this

Fifteenth Day of August, 2006

JON W. DUDAS
*Director of the United States Patent and Trademark Office*